United States Patent
Im et al.

(10) Patent No.: US 10,140,547 B2
(45) Date of Patent: Nov. 27, 2018

(54) METHOD FOR DETECTING MICROORGANISM HAVING FLUORESCENT CHARACTERISTICS WITH RESPECT TO SPECIFIC WAVELENGTH

(71) Applicant: KOREA OCEANIC AND ATMOSPHERIC SYSTEM TECHNOLOGY (KOAST), Seoul (KR)

(72) Inventors: Hyo Hyuc Im, Seoul (KR); Kyu Young Choi, Seoul (KR); Yeong Jin Lee, Seoul (KR); Tae Yoon Song, Incheon (KR)

(73) Assignee: KOREA OCEANIC AND ATMOSPHERIC SYSTEM TECHNOLOGY (KOAST), Seoul (KR)

( * ) Notice: Subject to any disclaimer, the term of this patent is extended or adjusted under 35 U.S.C. 154(b) by 232 days.

(21) Appl. No.: 15/028,811

(22) PCT Filed: Jun. 25, 2014

(86) PCT No.: PCT/KR2014/005610
§ 371 (c)(1),
(2) Date: Apr. 12, 2016

(87) PCT Pub. No.: WO2015/056863
PCT Pub. Date: Apr. 23, 2015

(65) Prior Publication Data
US 2016/0253572 A1  Sep. 1, 2016

(30) Foreign Application Priority Data
Oct. 15, 2013 (KR) .......... 10-2013-0122582

(51) Int. Cl.
*G06K 9/00* (2006.01)
*C12Q 1/06* (2006.01)
(Continued)

(52) U.S. Cl.
CPC ............. *G06K 9/4671* (2013.01); *C12Q 1/06* (2013.01); *G01N 15/1463* (2013.01);
(Continued)

(58) Field of Classification Search
CPC ..................... G06K 9/4671; G01N 15/1463
See application file for complete search history.

(56) References Cited

U.S. PATENT DOCUMENTS 4,097,845 A     6/1978  Bacus
4,972,258 A *  11/1990  Wolf .................. G02B 21/002
                                                          250/458.1
(Continued)

FOREIGN PATENT DOCUMENTS

JP    2007071742      3/2007
KR    1020120112890   10/2012

OTHER PUBLICATIONS

Chen, et al, "An Automatic Cell Counting Method for Optical Images", In: Proceedings of the first joint BMES/EMBS Conference, Oct. 1999, Atlanta, GA.

*Primary Examiner* — Jayanti K Patel
*Assistant Examiner* — Irfan Habib
(74) *Attorney, Agent, or Firm* — Lex IP Meister, PLLC (57) ABSTRACT

A method for determining a number of individuals of microorganisms included in a sample using an optical apparatus, comprising steps of: collecting, by the image acquisition unit, light radiated by microorganisms which radiate only light of a specific wavelength range and are included in the sample; generating, by the image acquisition unit, an image of the collected image; displaying, by the image
(Continued)

processing unit, the image generated by the image acquisition unit on a screen, analyzing each of pixels forming the screen on which the image has been displayed, and classifying a plurality of pixels which belongs to the pixels included in the screen and continuously emit light to be a single object; and calculating, by the image processing unit, a total number of objects classified in the screen.

3 Claims, 4 Drawing Sheets (51) Int. Cl.
- *G06K 9/46* (2006.01)
- *G01N 21/64* (2006.01)
- *G01N 15/14* (2006.01)
- *H04N 5/232* (2006.01)
- *G01N 15/00* (2006.01)
- *G01N 15/10* (2006.01)

(52) U.S. Cl.
CPC ....... *G01N 21/6456* (2013.01); *G06K 9/0014* (2013.01); *H04N 5/23229* (2013.01); *G01N 2015/0065* (2013.01); *G01N 2015/1006* (2013.01); *G01N 2015/1486* (2013.01); *G06K 9/00134* (2013.01)

(56) References Cited

U.S. PATENT DOCUMENTS

| | | | |
|---|---|---|---|
| 5,507,287 A * | 4/1996 | Palcic | A61B 1/00186 356/318 |
| 5,510,246 A * | 4/1996 | Morgan | C12Q 1/04 377/10 |
| 5,556,764 A | 9/1996 | Sizto et al. | |
| 6,096,272 A * | 8/2000 | Clark | G01N 21/253 422/64 |
| 6,243,492 B1 * | 6/2001 | Kamei | G06K 9/00087 382/124 |
| 6,539,115 B2 * | 3/2003 | Fujimoto | G06K 9/6857 382/225 |
| 6,780,581 B2 * | 8/2004 | Vesey | A01N 1/02 435/239 |
| 7,374,904 B2 * | 5/2008 | Vesey | C12N 1/005 435/30 |
| 7,531,319 B2 * | 5/2009 | Martin | C12Q 1/04 435/41 |
| 8,361,742 B2 * | 1/2013 | Martin | A61L 15/56 264/78 |
| 9,013,570 B2 * | 4/2015 | Matsunobu | G02B 21/125 348/79 |
| 9,034,593 B2 * | 5/2015 | Martin | A61B 5/14507 435/25 |
| 9,323,037 B2 * | 4/2016 | Yoshioka | G02B 21/16 |
| 9,354,147 B2 * | 5/2016 | Lefebvre | G01N 1/312 |
| 9,367,919 B2 * | 6/2016 | Choi | G06T 7/0044 |
| 9,513,404 B1 * | 12/2016 | Choi | G01W 1/18 |
| 9,665,940 B2 * | 5/2017 | Foelling | G01N 21/6458 |
| 9,838,614 B1 * | 12/2017 | Brailovskiy | H04N 5/247 |
| 9,856,446 B2 * | 1/2018 | Suslick | C12Q 1/04 |
| 10,023,895 B2 * | 7/2018 | Richards | B01L 3/527 |
| 2003/0170613 A1 * | 9/2003 | Straus | G01N 33/56916 435/5 |
| 2007/0269085 A1 * | 11/2007 | Oshiro | G02B 21/365 382/128 |
| 2008/0057533 A1 * | 3/2008 | Martin | C12Q 1/04 435/34 |
| 2009/0074275 A1 * | 3/2009 | O Ruanaidh | G06T 7/0081 382/128 |
| 2012/0244529 A1 * | 9/2012 | Fuchs | B01L 3/5027 435/6.11 |
| 2014/0343868 A1 * | 11/2014 | Colwell | G06F 19/22 702/20 |
| 2015/0293270 A1 * | 10/2015 | Jarvius | G02B 21/241 348/79 |
| 2016/0232422 A1 * | 8/2016 | Yoshioka | G02B 21/16 |
| 2016/0238826 A1 * | 8/2016 | Shields | G02B 7/38 |
| 2017/0355544 A1 * | 12/2017 | Matsumoto | B65H 5/062 |
| 2018/0107896 A1 * | 4/2018 | Sagong | G06T 7/187 |

* cited by examiner

METHOD FOR DETECTING MICROORGANISM HAVING FLUORESCENT CHARACTERISTICS WITH RESPECT TO SPECIFIC WAVELENGTH

BACKGROUND

The present invention relates to a method for checking the number of individuals regarding microorganisms included in a sample and, more particularly, to a method for examining microorganisms having a fluorescent characteristic with respect to a specific wavelength, which is capable of accurately calculating the number of individuals of microorganisms which are included in a sample and have a fluorescent characteristic with respect to a specific wavelength.

The present invention relates to a method for examining microorganisms.

In particular, in the case of microorganisms, such as plankton having a fluorescent characteristic for blue-series light having a wavelength of 380 nm to 480 nm, the check of the number of individuals of the microorganisms is treated as very important in order to protect a marine ecosystem from pollutions attributable to ballast water in addition to a detailed check and research for an algal bloom or red tide phenomenon.

The check of the number of individuals of microorganisms is measures for preventing damage to the marine ecosystem attributable to ballast water included in a vessel travelling between countries. If a vessel that has departed from a specific area discharges ballast water in order to lie in another area, processing for plankton included in the ballast water which may threaten the marine ecosystem of another area needs to be first performed.

In particular, in order to prevent ecological and economic damage which may be generated by a movement of ballast water and to preserve biological diversity, the International Maritime Organization (IMO) adopted "International Convention for the Control and Management of Ships' Ballast Water and Sediments (BWM)" on February 2004.

Specifically, methods which may be used to process ballast water according to the criteria of the adopted convention may be basically divided into two kinds. The first is an in-line processing method, and the second is an in-tank processing method. The in-line processing method is a method for processing ballast water when the ballast water is introduced and discharged. The in-tank processing method is a method for processing ballast water on the voyage after the ballast water is introduced. Current international ballast water processing technologies include the in-line processing method. In the in-tank processing method, the size of a processing apparatus may be reduced compared with the in-line processing method, but efficiency is practically reconsidered because processing speed needs to be conditioned by taking hours under way into consideration.

In both the methods, the number of individuals of problematic plankton included in ballast water is checked, a corresponding proper processing method is capable of being selected, and an examination regarding whether problematic plankton included in discharged ballast water has been processed according to criteria must be performed by performing the final examination for ballast water discharged before the processed ballast water is discharged.

However, an expert examination method for checking the number of individuals of microorganisms, such as problematic plankton included in ballast water, has not been provided so far.

In an existing method for examining microorganisms, such as plankton included in ballast water, only a method for photographing a sample and determining, by an expert, the number of individuals of problematic plankton included in the photographed sample by determining an image of the sample with the naked eye is performed. Such an existing method has a problem in that it is very difficult to accurately calculate the number of individuals of microorganisms, such as problematic plankton included in a sample.

Furthermore, an existing method for examining microorganisms including plankton has a problem in that it is difficult to check the accurate number of individuals of microorganisms because it is difficult to distinguish various alien substances from each other and to distinguish active microorganisms and inactive microorganisms from each other.

A background art of the present invention is disclosed in Korean Patent Application Publication No. 10-1995-7001601, etc., but does not suggest a solution for the aforementioned problems.

SUMMARY OF THE INVENTION

An object of the present invention made to solve the aforementioned problems is to provide a method for examining microorganisms having a fluorescent characteristic with respect to a specific wavelength, including steps (a) and (b) of collecting light reflected by microorganisms having a fluorescent characteristic with respect to a specific wavelength and generating an image of the collected light, a step (c) of analyzing the generated image and classifying a plurality of pixels continuously emitting light to be a single object, and a step (d) of calculating a total number of classified objects, thereby being capable of accurately calculating the number of individuals of microorganisms which are included in a sample and have a fluorescent characteristic with respect to a specific wavelength.

Furthermore, an object of the present invention is to provide a method for examining microorganisms having a fluorescent characteristic with respect to a specific wavelength, further including a step of classifying a plurality of pixels continuously emitting light to be a single object by introducing an edge detection processing method in the step (c), thereby being capable of checking the accurate number of individuals of microorganisms included in a sample.

Furthermore, an object of the present invention is to provide a method for examining microorganisms having a fluorescent characteristic with respect to a specific wavelength, further including a step of classifying only a plurality of pixels continuously emitting light within a range of a predetermined number of pixels to be a single object in the step (c), thereby being capable of checking the number of individuals of corresponding microorganisms more accurately through a filtering process for various alien substances included in a sample.

In accordance with a characteristic of the present invention for achieving the above objects, the present invention includes a method for determining the number of individuals of microorganisms included in a sample using an optical apparatus, including a light source unit for supplying light to the sample including the microorganisms which reflect only light of a specific wavelength range and have a fluorescent characteristic and a detection unit including an image acquisition unit for generating an image by collecting the light reflected by the microorganisms and an image processing unit for processing the generated image. The method including the steps of (a) collecting, by the image acquisition unit, light radiated by microorganisms which radiate only light of a specific wavelength range and are included in the sample; (b) generating, by the image acquisition unit, an image of the collected image; (c) displaying, by the image processing unit, the image generated by the image acquisition unit on a screen, analyzing each of pixels forming the screen on which the image has been displayed, and classifying a plurality of pixels which belongs to the pixels included in the screen and continuously emit light to be a single object; and (d) calculating, by the image processing unit, a total number of objects classified in the screen.

In this case, the step (c) includes a step (c-1) for performing, by the image processing unit, edge detection processing on the generated image and a step (c-2) for scanning the image subjected to the edge detection processing in the step (c-1) and classifying a plurality of pixels which is included in each of edge lines included in the edge detection-processed image and which continuously emits light to be the single object.

Furthermore, in the step (c), the image processing unit classifies only an object belonging to the objects and having the number of pixels forming the single object within a range of a predetermined number to be a target object, and in the step (d), the total number of objects included in the screen and calculated by the image processing unit is a total number of target objects.

Furthermore, in the step (c), the image processing unit classifies the plurality of pixels continuously emitting light to be the single object, wherein the image processing unit determines only a plurality of pixels which continuously emits light within a range of a predetermined contrast range along with one or more of all of neighboring pixels with respect to the pixels forming the screen to be the single object.

In accordance with the present invention, such as that described above, there can be provided a method for examining microorganisms having a fluorescent characteristic with respect to a specific wavelength, which is capable of accurately calculating the number of individuals of microorganisms which are included in a sample and have a fluorescent characteristic with respect to a specific wavelength.

Furthermore, in accordance with the present invention, there can be provided a method for examining microorganisms having a fluorescent characteristic with respect to a specific wavelength, which is capable of checking the accurate number of individuals of microorganisms included in a sample.

Furthermore, there can be provided a method for examining microorganisms having a fluorescent characteristic with respect to a specific wavelength, which is capable of checking the number of individuals of corresponding microorganisms more accurately through a filtering process for various alien substances included in a sample.

DESCRIPTION OF REFERENCE NUMERALS

100: optical apparatus applied to method for examining microorganisms having fluorescent characteristic with respect to specific wavelength according to the present invention
110: optical filter unit
111: excitation filter
112: dichroic mirror
120: detection unit
121: image acquisition unit
122: image processing unit
130: light induction member
141, 142, 143: support member
150: light source unit
190: stage

DESCRIPTION OF THE PREFERRED EMBODIMENTS

The merits and characteristics of the present invention and a method for achieving the merits and characteristics will become more apparent from embodiments described in detail in conjunction with the accompanying drawings.

However, the present invention is not limited to the disclosed embodiments, but may be implemented in various different ways. The embodiments are provided to only complete the disclosure of the present invention and to allow those skilled in the art to understand the category of the present invention. The present invention is defined by the category of the claims. The same reference numbers will be used to refer to the same or similar elements throughout the drawings.

Methods for examining microorganisms having a fluorescent characteristic with respect to a specific wavelength according to embodiments of the present invention are described below with reference to the drawings.

Figure 1:
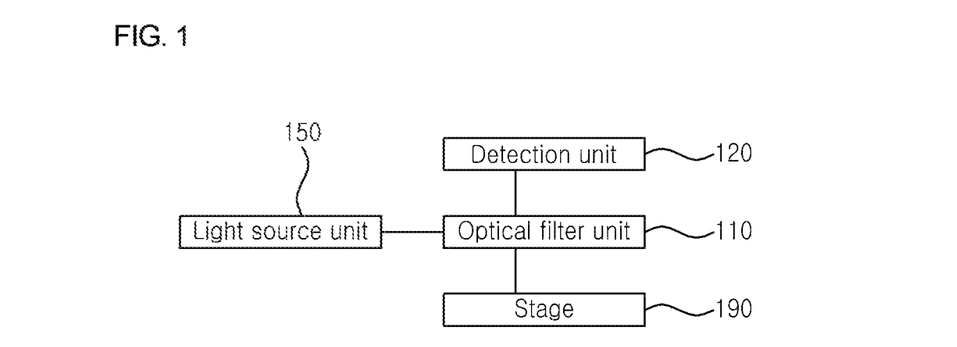
FIG. 1 is a schematic block diagram regarding an optical apparatus which performs a method for examining microorganisms having a fluorescent characteristic with respect to a specific wavelength according to the present invention.
Figure 2:
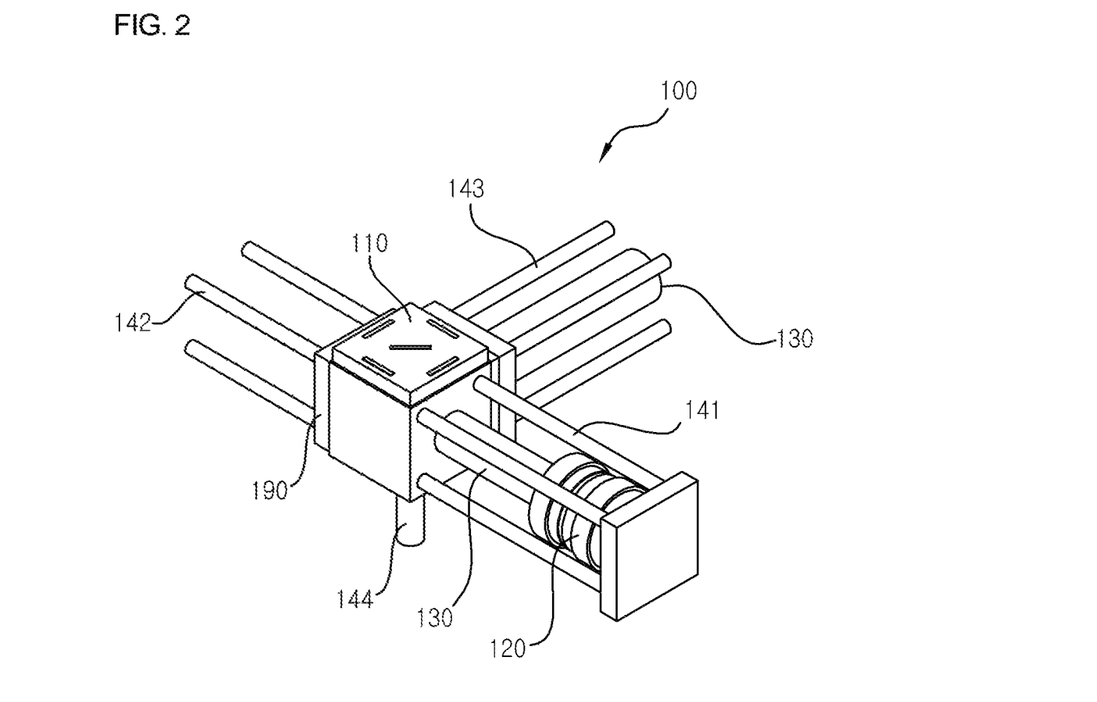
FIG. 2 is a perspective view for illustrating the internal configuration of the optical apparatus.
Figure 3:
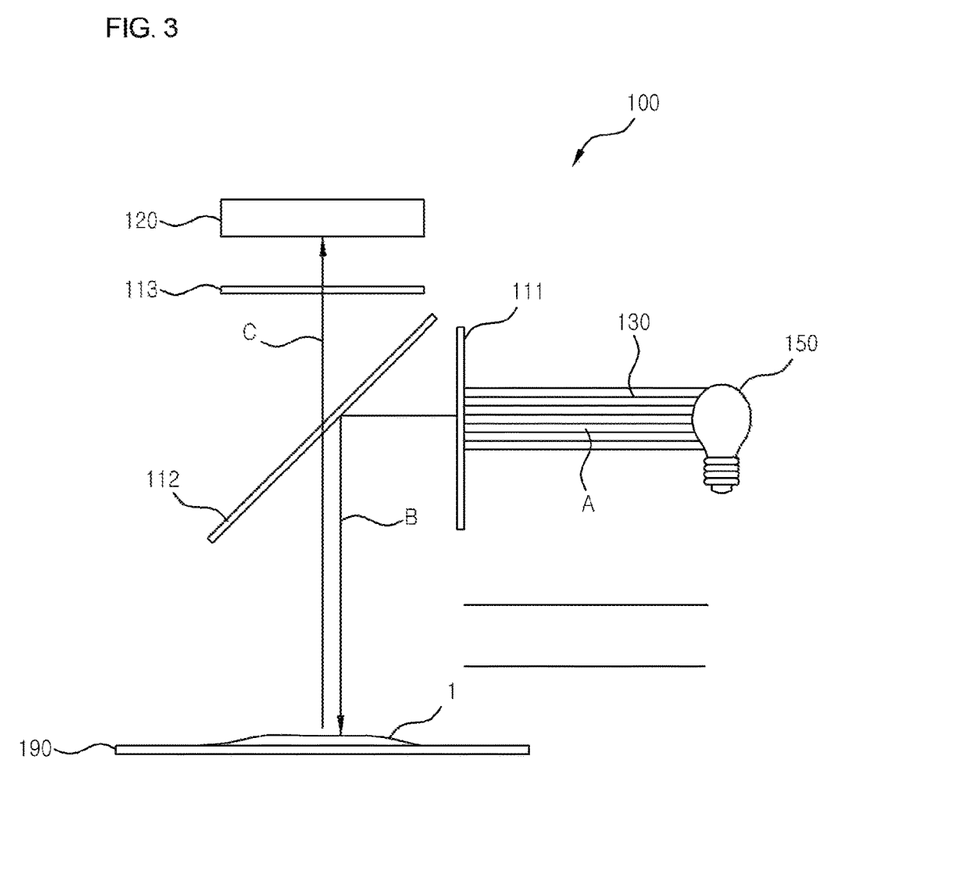
FIG. 3 is an explanatory diagram for illustrating the structure of the optical apparatus.
Figure 4:
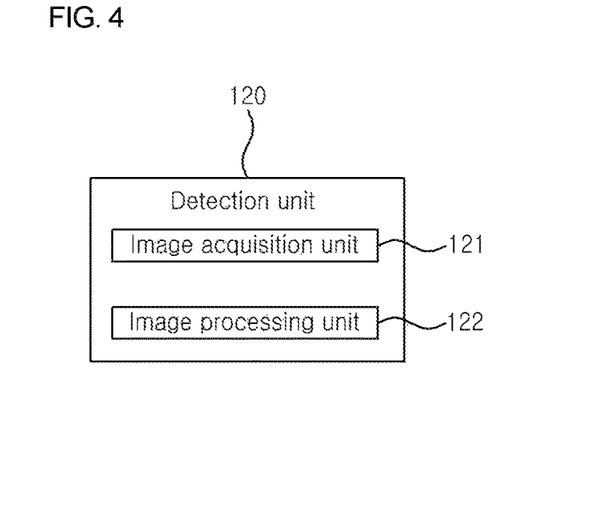
FIG. 4 is a block diagram of a detection unit.

FIG. 1 is a schematic block diagram regarding an optical apparatus which performs a method for examining microorganisms having a fluorescent characteristic with respect to a specific wavelength according to the present invention, FIG. 2 is a perspective view for illustrating the internal configuration of the optical apparatus, FIG. 3 is an explanatory diagram for illustrating the structure of the optical apparatus, and FIG. 4 is a block diagram of a detection unit.

Figure 5:
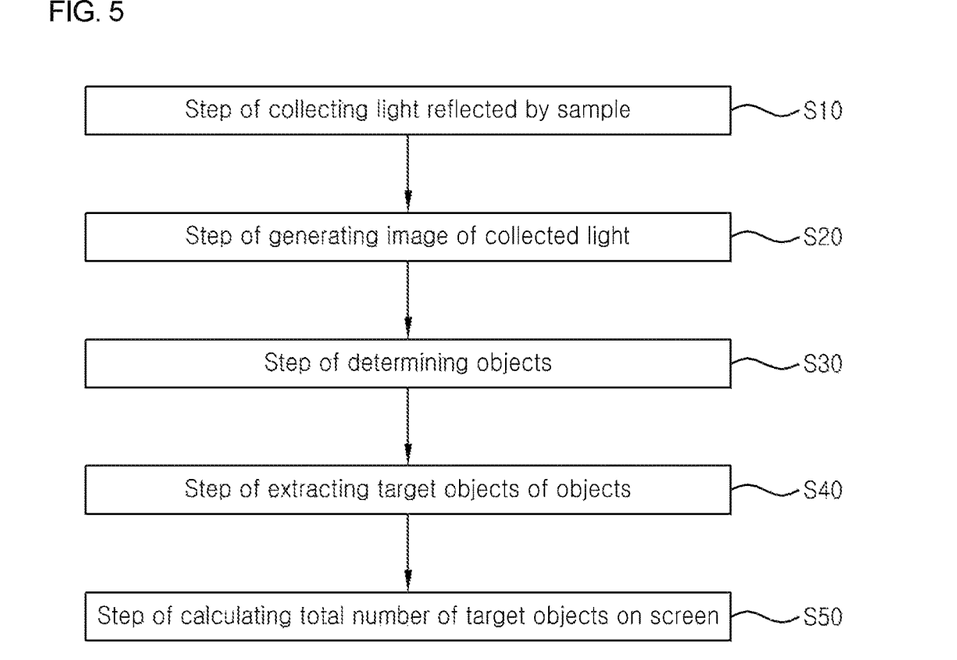
FIGS. 5 and 6 are flowcharts for methods for examining microorganisms having a fluorescent characteristic with respect to a specific wavelength according to the present invention.
Figure 6:
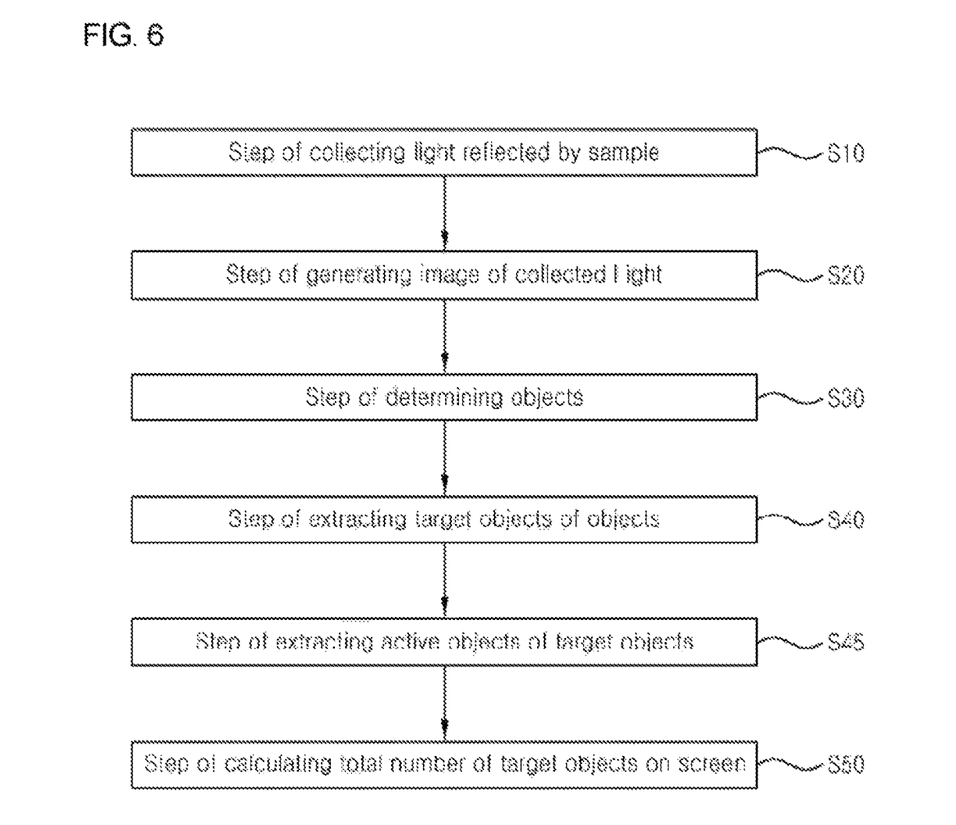

Furthermore, FIGS. 5 and 6 are flowcharts of methods for examining microorganisms having a fluorescent characteristic with respect to a specific wavelength according to the present invention.

A method for examining microorganisms having a fluorescent characteristic with respect to a specific wavelength according to a preferred embodiment of the present invention relates to a method for determining the number of individuals of microorganisms included in a sample using an optical apparatus 100, including a light source unit 150 for supplying light to a sample including microorganisms which reflect only light of a specific wavelength range and have a fluorescent characteristic and a detection unit 120 including an image acquisition unit 121 for generating an image by collecting the light reflected by the microorganisms and an image processing unit 122 for processing the generated image.

First, the construction of the optical apparatus 100 used in a method for examining microorganisms having a fluorescent characteristic with respect to a specific wavelength according to the present invention is described.

The optical apparatus 100, as shown in FIGS. 1 to 3, includes the light source unit 150, an optical filter unit 110, a stage 190, and the detection unit 120.

The light source unit 150 is means for performing the function of a light source used in an optical microscope, etc. and is mainly means for emitting a visible ray or light of a specific wavelength band.

When light of the entire visible ray band is generated by the light source unit 150, the optical filter unit 110 may include an excitation filter 111 for transmitting only light of a specific wavelength band that belongs to the emitted light of the visible ray band and enables microorganisms to indicate a fluorescent characteristic through filtering and for delivering the light of the specific wavelength band to the stage 190.

In this case, a light source that emits only the light of the specific wavelength band in which the microorganisms indicate the fluorescent characteristic may be used as the light source unit 150. In this case, the aforementioned excitation filter may be excluded.

An example of microorganisms indicative of a fluorescent characteristic with respect to light of the specific wavelength band includes plankton including chlorophyll, etc.

The plankton is microorganisms having a fluorescent characteristic for red-series light having a wavelength of 620 nm to 780 nm. In this specification, the phytoplankton is described as an example.

The stage 190 is a support on which a sample, such as ballast water or seawater, is disposed. It is preferred that the sample is disposed on the stage in the state in which ballast water, seawater or the like has been filtered.

The detection unit 120 is means for collecting reflected light reflected by the sample which is disposed on the stage 190 and receives light from the light source unit 150 and detecting an image of the sample. The detection unit 120 includes a camera used in an optical microscope.

In this case, it is preferred that a camera capable of monitoring the subject of the least 10 μm is used as the camera used in the detection unit 120. It is preferred that the camera used in the detection unit 120 has resolution of 1250*1250 pixels or more.

That is, the detection unit 120 is means for detecting an image of the sample disposed on the stage 190 by focusing light reflected by the sample. The detection unit 120 is disposed at the place opposite the stage 190 in such a way as to receive light emitted by the light source unit 150 and to detect an image of plankton included in the sample by focusing light reflected by plankton included in the sample.

The optical filter unit 110 is means for delivering light, provided by the light source unit 150, to the sample disposed on the stage 190 and delivering light, reflected by the sample, to the detection unit 120.

In this case, it is preferred that light paths are connected between the light source unit 150, the optical filter unit 110, the detection unit 120, and the stage 190 so that the light of the light source unit 150 moves to the sample on the stage 190 through the optical filter unit 110 without interfering with external light and the light reflected by the sample moves to the detection unit 120 through the optical filter unit 110 without interference.

The optical filter unit 110 includes the excitation filter 111 and a dichroic mirror 112.

The excitation filter 111 is a filter for transmitting only light that belongs to light emitted by the light source unit 150 and has blue-series of 380 nm to 480 nm.

In this case, the excitation filter may be excluded from the light source unit if the optical filter unit 110 is configured so that the microorganisms emit only light of a specific wavelength indicative of a fluorescent characteristic.

The dichroic mirror 112 is means for delivering blue-series light, passing through the excitation filter 111, to the sample disposed on the stage and delivering light, reflected by the sample, to the detection unit 120.

The stage 190 and the detection unit 120 are disposed in a straight line, and the light source unit 150 is disposed in the direction crossing the straight line that connects the detection unit 120 and the stage 190.

In this case, the dichroic mirror 112 is an optical filter for reflecting blue-series light, that is, light passing through the excitation filter 111, to the sample on the stage 190 and transmitting only red-series light reflected by the sample without any change (i.e., without reflection or reflection or both) so that the red-series light is focused on the detection unit 120.

That is, the excitation filter 111 transmits only blue-series light having a wavelength of 380 nm to 480 nm. The dichroic mirror 112 reflects the blue-series light toward the sample on the stage 190 and transmits red-series light having a wavelength of 620 nm to 780 nm, that is, light reflected by the sample, toward the detection unit 120 in its travel direction without any change.

That is, the dichroic mirror 112 is an optical filter for reflecting light of 380 nm to 480 nm and transmitting light of 620 nm to 780 nm.

That is, the optical filter unit 110 is an element disposed between the light source unit 150 and the detection unit 120 and modulated so that the excitation filter 111 and the dichroic mirror 112 may perform the aforementioned functions.

Sides facing the light source unit 150, the stage 190, and the detection unit 120, respectively, are formed in the optical filter unit 110. Each of the sides includes an optical box in which an optical passage having light pass therethrough has been formed in the form of a through hole.

In this case, the excitation filter 111 is coupled to an optical passage that belongs to the optical passages of the optical boxes and that is formed in the side opposite the light source unit 150. The dichroic mirror 112 may be installed within the optical box so that the dichroic mirror 112 reflects light, passing through the excitation filter, toward the sample on the stage 190 and transmits light, reflected by plankton included in the sample, toward the detection unit 120.

In this case, it is preferred that an emission filter 113 is further included on the side that belongs to the sides of the optical boxes and that faces the detection unit 120.

The emission filter 113 is an optical filter for transmitting only light of a 600 nm wavelength or more and is a filter for minimizing the transfer of light, corresponding to noise, toward the detection unit.

It is preferred that the apparatus further includes a light induction member 130 of a pipe form which connects the light source unit 150 and the excitation filter coupled to the optical box so that light emitted by the light source unit 150 is concentrated on the excitation filter coupled to the optical box.

The light induction member 130 functions to allow light of the light source unit 150 to pass through the excitation filter 111 of the optical filter unit 110 purely without interference with external light.

Furthermore, it is preferred that the apparatus further includes a separate light induction member for connecting the optical filter unit 110, the stage 190, and the detection unit 120.

The detection unit 120 includes the image acquisition unit 121 for detecting light reflected by plankton included in the sample and generating an image of the plankton included in the sample and the image processing unit 122 for determining the number of plankton included in the sample by analyzing each of pixels included in a screen on which the generated image is displayed.

That is, the light of the light source unit 150 is delivered to microorganisms which reflect only light of a specific wavelength range and which are included in the sample disposed on the stage through the optical filter unit 110. After the light is reflected by the microorganisms, the reflected light is focused on the image acquisition unit 121 of the detection unit 120 through the optical filter unit 110, thereby generating an image of the microorganisms. The image processing unit 122 calculates the number of microorganisms included in the sample by processing the generated image.

Methods for examining microorganisms having a fluorescent characteristic with respect to a specific wavelength according to the present invention are described below.

In a method for determining the number of individuals of microorganisms included in a sample using the optical apparatus 100, including the light source unit 150 for supplying light to a sample including microorganisms which reflect only light of a specific wavelength range and have a fluorescent characteristic and the detection unit including the image acquisition unit 121 for generating an image by collecting the light reflected by the microorganisms and the image processing unit 122 for processing the generated image, a method for examining microorganisms having a fluorescent characteristic with respect to a specific wavelength according to the present invention includes a step (a) of collecting, by the image acquisition unit, light reflected by microorganisms which reflect only light of a specific wavelength range and are included in the sample, a step (b) of generating, by the image acquisition unit, an image of the collected image, a step (c) of displaying, by the image processing unit, the image generated by the image acquisition unit on a screen, analyzing each of pixels forming the screen on which the image has been displayed, and classifying a plurality of pixels which belongs to the pixels included in the screen and continuously emit light to be a single object, and a step (d) of calculating, by the image processing unit, a total number of objects classified in the screen.

That is, the method for examining microorganisms having a fluorescent characteristic with respect to a specific wavelength according to the present invention includes the step (step (a)) for first collecting, by the image acquisition unit 121, the light radiated by the microorganisms which radiate only the light of the specific wavelength range and are included in the sample and the step (step (b)) for generating, by the image acquisition unit, the image of the collected light.

For example, if the microorganisms are phytoplankton, when blue-series light that passes through the excitation filter 111 and has a wavelength of 380 nm to 480 nm is reflected toward the sample by the dichroic mirror 112, the energy level of the light having the wavelength of 380 nm to 480 nm is converted into that of light having a wavelength of 620 nm to 780 nm through the activity of photosynthesis of chlorophyll included in the phytoplankton, and the light having a wavelength of 620 nm to 780 nm is radiated. In this case, the dichroic mirror 112 transmits the radiated light having the wavelength of 620 nm to 780 nm toward the detection unit without any change. Accordingly, the image acquisition unit of the detection unit generates an image of the phytoplankton included in the sample, that is, the subject of detection.

Next, the image processing unit 122 displays the image, generated by the image acquisition unit, on the screen, analyzes each of the pixels forming the screen on which the image has been displayed, and classifies a plurality of pixels that belongs to the pixels included in the screen and that continuously emits light to be a single object (step (c)).

For example, if 2 pixels (a first object), 5 pixels (a second object), 12 pixels (a third object), and 20 pixels (a fourth object) each of which continuously emits light are present in the screen, the 4 objects are determined to be present in the screen.

Finally, the image processing unit 122 calculates the total number of objects included in the screen (step (d)).

That is, as described above, in the example, the 4 objects are calculated as being included in the screen for the sample.

In the step (c), it is natural that a method for determining, by the image processing unit 122, a plurality of pixels that continuously emits light may be easily extracted from information about the emitting pixels.

In this case, in the present invention, the image processing unit 122 determines pixels that continuously emit light using edge detection processing for the image.

An edge, that is, a contour line, means a line, that is, a characteristic indicative of the edge of a region within an image.

In this case, the edge detection is a method for obtaining pixels corresponding to a contour line based on a discontinuous point in brightness of an edge (i.e., a contour line) image. An existing edge detection processing method may be applied to the edge detection.

That is, the step (c) may include a step (c-1) for performing, by the image processing unit 122, edge detection processing on the generated image and a step (c-2) for scanning the image subjected to the edge detection processing in the step (c-1) and classifying a plurality of pixels which is included in each of edge lines included in the edge detection-processed image and continuously emits light to be the single object.

Objects included in the image can be extracted more accurately by classifying the objects using the edge detection method.

In this case, in the step (c), a limit may be set so that the image processing unit 122 classifies only the number of pixels which form one of the objects and are included within a range of a predetermined number to be a target object.

In this case, in the step (d), the total number of objects calculated by the image processing unit 122 and included in the screen may be a total number of the target objects.

This is for excluding floating matters, etc. other than plankton to be actually detected by previously setting the range of the number of continuous pixels corresponding to the size of actually problematic target plankton.

In the example, if actually problematic microorganisms have the range of the number of 4~13 pixels, the first object and the fourth object are excluded from the actually problematic microorganisms, and only the second object and the third object will be extracted as target objects.

Furthermore, in the step (c), the image processing unit may be configured to classify the plurality of pixels that continuously emits light to be the single object, but to determine only a plurality of pixels that continuously emits light within a range of a predetermined contrast range along with one or more of all of neighboring pixels with respect to the pixels forming the screen to be the single object.

That is, although 10 pixels continuously emit light, if 2 of the 10 pixels emit lights out of a predetermined contrast range with respect to all of neighboring pixels, only the 8 pixels other than the 2 pixels are determined to form a single object.

This is for extracting the target active object accurately by extracting the number of pixels forming the single object accurately.

The method for examining microorganisms having a fluorescent characteristic with respect to a specific wavelength according to the present invention may be configured to detect only microorganisms that belong to microorganisms included in a sample and that are actually alive and in activity, that is, active microorganisms.

That is, the method for examining microorganisms having a fluorescent characteristic with respect to a specific wavelength according to the present invention may further include a step for extracting only an object that belongs to the objects classified by the image processing unit 122 in the step (c) and that has an average brightness value of the pixels forming the objects, corresponding to a predetermined brightness range, as an active object.

That is, in the example, if the intensity range of brightness of light for the microorganisms that are actually active, that is, that are in activity as actual living organisms, for example, is a range of 10 luces to 20 luces and the range of brightness predetermined in the image processing unit is 10 luces to 20 luces, assuming that average brightness of the pixels forming the first object is 8 luces, average brightness of the pixels forming the second object is 10 luces, average brightness of the pixels forming is 16 luces, and average brightness of the pixels forming the fourth object is 25 luces, the image processing unit 122 extracts only the second and the third objects of the first to the fourth objects as active objects.

That is, the two active objects are determined to be present in the screen.

In this case, a certain range of the predetermined brightness or intensity of light may be set using various existing units for brightness or intensity of light, such as lumen (the speed of light) or lux (luminous intensity), or a candela (cd).

Furthermore, the detection unit digitizes the image of the collected light and represents the image so that it has a value between 0 at which brightness of each of the pixels forming the image has not been actually detected and 256 at which brightness of each of the pixels forming the image has the greatest brightness of light. A certain range of the predetermined brightness or intensity of light may be previously set in a range of a proper value between the values 0 to 256.

In this case, the total number of microorganisms calculated in the step (d) may be the number of active objects.

In this case, if the step (c) further includes the step for classifying, by the image processing unit 122, one of the objects which has only the number of pixels included within the range of the predetermined number to be a target object, the target objects finally calculated in the step (d) may be a total number of target active objects, that is, microorganisms satisfying both the conditions of the active object and the target object.

The method for examining microorganisms having a fluorescent characteristic with respect to a specific wavelength according to the present invention has an advantage in that only the number of individuals of pure microorganisms which are included in a sample including microorganisms having a fluorescent characteristic for light of a specific wavelength, for example, plankton and from which alien substances other than the corresponding microorganisms have been filtered through the aforementioned construction.

An apparatus for examining microorganisms having a fluorescent characteristic with respect to a specific wavelength according to the present invention is described below.

The apparatus for examining microorganisms having a fluorescent characteristic with respect to a specific wavelength includes the light source unit 150 which emits light; the stage 190 on which a sample that is an object to be detected and that includes microorganisms having a fluorescent characteristic with respect to a specific wavelength is disposed; the detection unit 120 which is disposed at the place facing the stage 190 in such a way as to receive light emitted by the light source unit 150 and to generate an image of the microorganisms included in the sample by focusing light reflected by the microorganisms included in the sample; and the optical filter unit 110 which includes the excitation filter 111 delivering the light emitted by the light source unit 150 toward the sample disposed on the stage 190, delivering the light reflected by the sample toward the detection unit 120, but transmitting only blue-series light that belongs to the light emitted by the light source unit 150 and that has a wavelength of 380 nm to 480 nm and the optical filter 112 reflecting the light passing through the excitation filter toward the sample on the stage 190 and transmitting only red-series light that belongs to the light reflected by the microorganisms included in the sample and that has a wavelength of 620 nm to 780 nm toward the detection unit 120.

In this case, the sides facing the light source unit 150, the stage 190, and the detection unit 120, respectively, are formed in the optical filter unit 110. Each of the sides includes the optical box in which the optical passage having light pass therethrough is formed. The excitation filter 111 is coupled to an optical passage that belongs to the optical passages of the optical boxes and that is present in the side facing the light source unit 150. The dichroic mirror 112 is installed within the optical box in such a way as to reflect light passing through the excitation filter toward the sample on the stage 190 and to transmit light reflected by plankton included in the sample toward the detection unit 120.

Furthermore, the apparatus may further include the light induction member 130 of a pipe form which connects the light source unit 150 and the excitation filter coupled to the optical box so that light emitted by the light source unit 150 is focused on the excitation filter coupled to the optical box.

Furthermore, the detection unit 120 includes the image acquisition unit 121 which detects light reflected by plankton included in the sample, generates an image of the microorganisms included in the sample, and displays the image on a screen; and the image processing unit 122 which determines the number of microorganisms included in the sample by analyzing each of pixels included in the screen on which the generated image has been displayed, determines a plurality of pixels that belongs to the pixels included in the screen and that continuously emits light to be a single object, calculates a total number of objects included in the screen, and determines the total number of objects to be a total number of target microorganisms included in the screen.

Furthermore, the image processing unit 122 determines only corresponding objects that belong to the objects and that have the number of a plurality of pixels continuously emitting light within a range of a predetermined number to be target microorganisms, that is, microorganisms to be actually detected, calculates a total number of target microorganisms included in the screen, and determines the calculated total number of target microorganisms to be a total number of target microorganisms included in the screen.

Furthermore, the image processing unit 122 excludes an object that belongs to the objects determined to be the target microorganisms and that has a predetermined intensity range of light out of an average intensity value of light of all of pixels forming a single object from the target microorganisms.

Furthermore, the image processing unit 122 performs processing so that the plurality of pixels that is determined to be the single object and continuously emits light includes only neighboring pixels and pixels continuously emitting light within a predetermined contrast range.

The apparatus for examining microorganisms may further include a communication unit connected to the detection unit 120 and capable of receiving an image of plankton generated by the image acquisition unit 121 and/or information about a total number of target plankton calculated by the image processing unit 122 and transmitting the image and information to a separate examination and check system.

Furthermore, the apparatus may further include a display unit connected to the detection unit 120 and for displaying an image of plankton generated by the image acquisition unit 121 and/or information about a total number of target plankton calculated by the image processing unit 122.

Those skilled in the art to which the present invention pertains will appreciate that the present invention may be implemented in other detailed forms without departing from the technical spirit or essential characteristics of the present invention. Accordingly, the aforementioned embodiments should be understood as being only illustrative, but should not be understood as being restrictive from all aspects. The scope of the present invention is defined by the following claims rather than the detailed description, and the meanings and scope of the claims and all changes or modified forms derived from their equivalents should be construed as falling within the scope of the present invention.

What is claimed is:

1. A method for determining a number of individuals of microorganisms included in a sample using an optical apparatus, comprising a light source unit for supplying light to a sample comprising microorganisms which reflect only light of a specific wavelength range and have a fluorescent characteristic and a detection unit comprising an image acquisition unit for generating an image by collecting the light reflected by the microorganisms and an image processing unit for processing the generated image, the method comprising steps of:
    (a) collecting, by the image acquisition unit, light radiated by microorganisms which radiate only light of a specific wavelength range and are included in the sample;
    (b) generating, by the image acquisition unit, an image of the collected image;
    (c) displaying, by the image processing unit, the image generated by the image acquisition unit on a screen, analyzing each of pixels forming the screen on which the image has been displayed, classifying a plurality of pixels which belongs to the pixels included in the screen and continuously emit light as a single object, and extracting only an object that belongs to said single object and has an average brightness value of the pixels forming the object, corresponding to a predetermined brightness range, as an active object; and wherein in the step (c), the image processing unit classifies the plurality of pixels continuously emitting light to be the single object, wherein the image processing unit determines only a plurality of pixels which continuously emits light within a range of a predetermined contrast range along with one or more of all of neighboring pixels with respect to the pixels forming the screen to be the single object;
    (d) calculating, by the image processing unit, a total number of active objects classified in the screen.

2. The method of claim 1, wherein in the step (c), the image processing unit performs edge detection processing on the generated image.

3. The method of claim 1, wherein:
in the step (c), the image processing unit classifies only an object belonging to the objects and having the number of pixels forming the single object within a range of a predetermined number to be a target object, and
in the step (d), the total number of objects included in the screen and calculated by the image processing unit is a total number of target objects.

* * * * *